United States Patent [19]

Inoue et al.

[11] Patent Number: 4,965,350

[45] Date of Patent: Oct. 23, 1990

[54] PYRIDOPYRIMIDINE NUCLEOTIDE COMPOUNDS

[75] Inventors: Hideo Inoue; Eiko Ohtsuka, both of Sapporo; Akihiro Imura, Tokyo; Kenichi Masuda, Hachioji; Takashi Kamimura, Tokyo, all of Japan

[73] Assignee: Teijin Limited, Osaka, Japan

[21] Appl. No.: 351,317

[22] Filed: May 11, 1989

Related U.S. Application Data

[63] Continuation of Ser. No. 54,910, filed as PCT JP86/00441 on Aug. 26, 1986, published as WO87/01373 on Mar. 12, 1987, abandoned.

[30] Foreign Application Priority Data

Sep. 9, 1985 [JP] Japan .................... 60-197689

[51] Int. Cl.$^5$ .............................. A61K 31/70
[52] U.S. Cl. ........................ 536/28; 536/27; 536/29
[58] Field of Search .................... 536/24, 28

[56] References Cited

U.S. PATENT DOCUMENTS

4,711,955 12/1987 Ward et al. ................. 536/26

FOREIGN PATENT DOCUMENTS

0063879 11/1982 European Pat. Off. ............. 536/23

OTHER PUBLICATIONS

Bergstrom et al., J. Org. Chem. 47, 2174–2178 (1982).
Schattenkerk et al., Nucleic Acid Research, 11 (No. 21) pp. 7545–7554 (1983).

*Primary Examiner*—Ronald W. Griffin
*Assistant Examiner*—James O. Wilson
*Attorney, Agent, or Firm*—Sughrue, Mion, Zinn, Macpeak & Seas

[57] ABSTRACT

Pyridopyrimidine nucleotide derivatives expressed by formula (I), which are fluorescent and capable of forming base pairing with guanine or adenine, and oligo- or polynucleotide which have at least one of these derivatives in their molecules or at their molecular terminals:

(I)

wherein $X_1$ and $X_1$ respectively represent $$HO \!-\!\!\!\left(\!\!\!\begin{array}{c} O \\ \| \\ P\!-\!O \\ | \\ OH \end{array}\!\!\!\right)_{\!\!\overline{n}}$$

(in which n indicates an integer of 0, 1, 2, or 3; however, in no case $X_1$ and $Y_1$ both indicate n=0); $Z_1$ indicates a hydrogen atom or $$HO \!-\!\!\!\left(\!\!\!\begin{array}{c} O \\ \| \\ P\!-\!O \\ | \\ OH \end{array}\!\!\!\right)_{\!\!\overline{m}}\!\!-$$

(in which n indicates an integer of 1, 2, or 3); $W_1$ indicates a hydrogen atom or a hydroxyl group. As for $R_1$ and $R_2$, in case where $R_1$ is an amino group or halogen, $R_2$ indicates a single bond between the carbon atom at the 7-position and the nitrogen atom at the 8-position, and in case where $R_2$ is a hydrogen atom or an lower alkyl group, $R_1$ indicates a carbonyl bond $$\left(\!\!\begin{array}{c} \diagdown \\ \diagup \end{array}\!\! C\!=\!O\right)$$

formed with the carbon atom at the 7-position.

4 Claims, 5 Drawing Sheets

Fig. 3
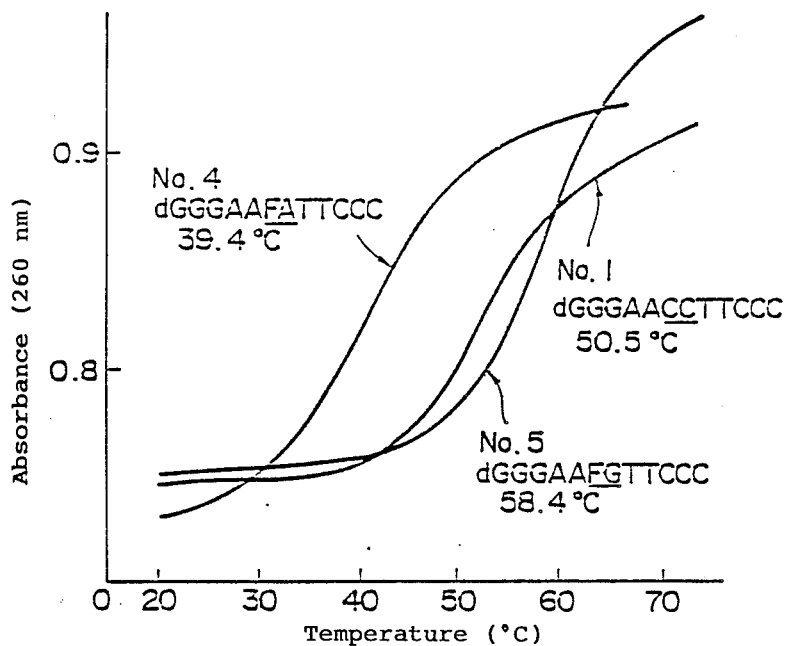
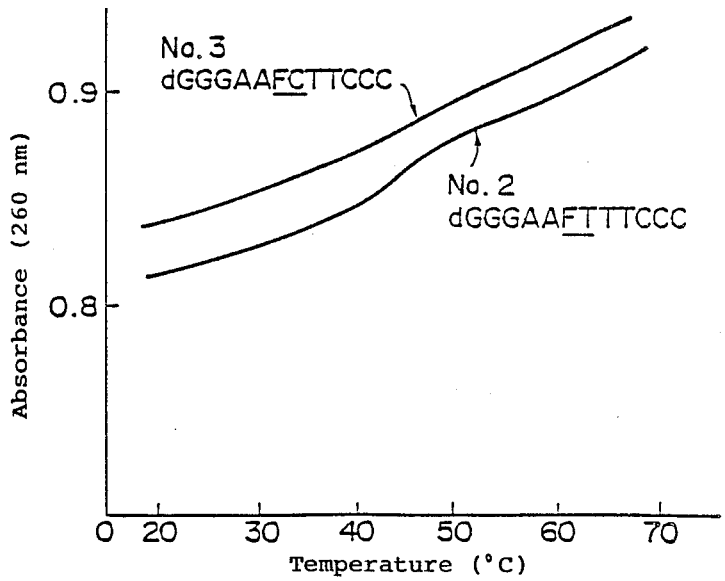

PYRIDOPYRIMIDINE NUCLEOTIDE COMPOUNDS

This is a continuation of application Ser. No. 07/054,910, filed as PCT JP86/00441 on Aug. 26, 1986, published as WO87/01373 on Mar. 12, 1987, now abandoned.

TECHNICAL FIELD

This invention relates to pyridopyrimidine nucleotide derivatives and oligo- or polynucleotides having any of such derivatives in their molecules or at their molecular terminals.

BACKGROUND ART

With the object of clarifying the correlation between the structure and function of biopolymers, especially that of proteins and nucleic acids, researches by means of the fluorescent probes are widely conducted. For conducting the research works on the nucleic acids, methods generally practiced, including one in which a very small amount of fluorescent base existing in the nucleic acid is used as a probe and another in which a fluorescent molecule is introduced chemically into the nucleic acid to be used as a probe. As the examples of nucleoside which has a fluorescent base, there are fluorescent etheno derivatives, expressed by the following formulas, which are obtained by treating adenosine or cytidine with chloroacetaldehyde:

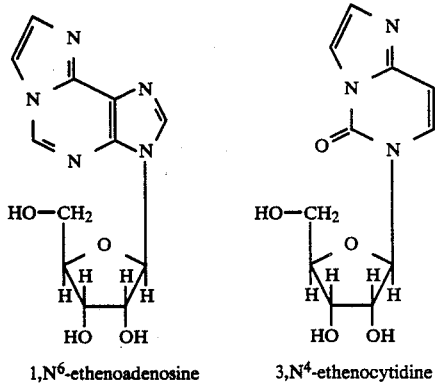

1,$N^6$-ethenoadenosine    3,$N^4$-ethenocytidine

The ethenoadenosine has especially been used in various studies as the fluorescent probe because of its strong fluorescence intensity in neutral condition; unfortunately, it is not capable of forming the complementary base pairing.

DISCLOSURE OF INVENTION

As the result of strenuous studies intended to obtain pyrimidine nucleotide derivatives which have fluorescence property and are capable of forming the complementary base pairing with guanine or adenine, the present inventors have completed this invention.

More particularly, this invention relates to pyridopyrimidine nucleotide derivatives expressed by formula (I):

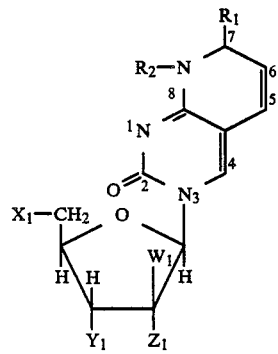

wherein $X_1$ and $Y_1$ respectively represent

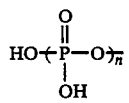

(in which n indicates an integer of 0, 1, 2, or 3; however, in no case $X_1$ and $Y_1$ both indicate n=0); $Z_1$ indicates a hydrogen atom or

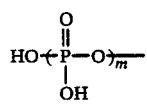

(in which m indicates an integer of 1, 2, or 3); $W_1$ indicates a hydrogen atom or a hydroxyl group. As for $R_1$ and $R_2$, in case where $R_1$ is an amino group or halogen, $R_2$ indicates a single bond between the carbon atom at the 7-position and the nitrogen atom at the 8-position, and in case where $R_2$ is a hydrogen atom or a lower alkyl group, $R_1$ indicates a carbonyl bond

formed with the carbon atom at the 7-position;) and oligo- or polynucleotides, which have at least one fluorescent nucleotide expressed by formula (II), in their molecules or at their molecular terminals.

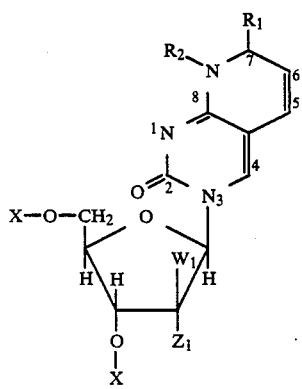

wherein X is hydrogen, a nucleotide or —$PO_3H$;

wherein $W_1$ represents a hydrogen atom or a hydroxyl group;

wherein $Z_1$ represents a hydrogen atom or a hydroxyl group;

however in no case do both $W_1$ and $Z_1$ represent a hydroxyl group;

wherein $R_1$ represents an amino group or halogen and $R_2$ represents a single bond between the carbon atom at the 7-position and the nitrogen atom at the 8-position or $R_1$ represents a carbonyl bond

formed with the carbon atom at the 7-position and $R_2$ represents a hydrogen atom or a lower alkyl group.

BRIEF DESCRIPTION OF DRAWINGS

FIGS. 3 and 4 show the absorption-temperature profiles of oligonucleotides containing pyridopyrimidine nucleotide of this invention.

BEST MODE OF CARRYING OUT THE INVENTION

Figure 1:
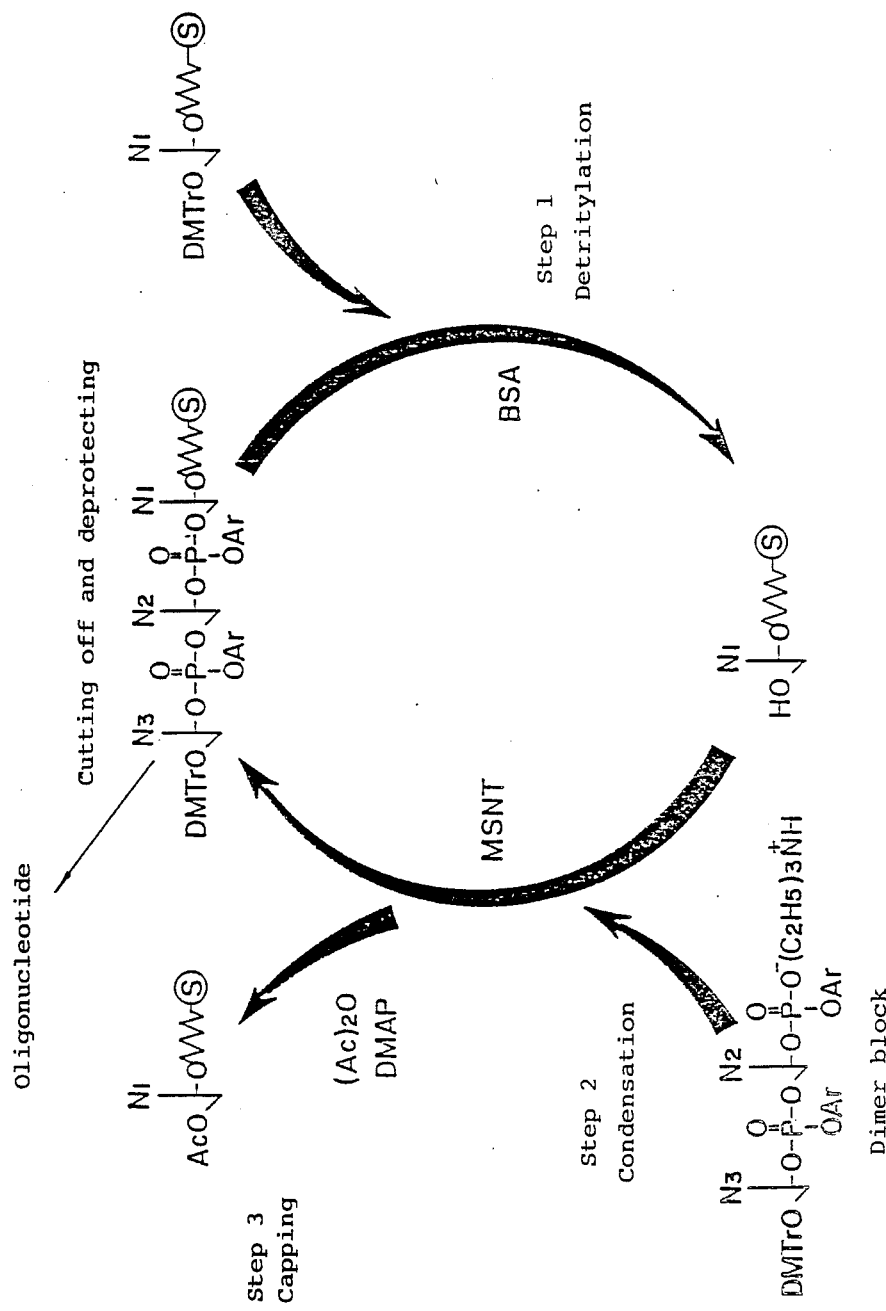
FIG. 1 shows a procedure of synthesis of oligonucleotide through the phosphotriester solid-phase method.

Of the compounds expressed by formula (I) according to this invention, an especially desirable one is a compound in which $X_1$ and/or $Y_1$ is

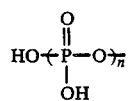

(wherein n indicates an integer of 1, 2, or 3); $Z_1$ is a hydrogen atom or a hydroxyl group; and $W_1$ is a hydrogen atom.

These compounds in which the hydroxyl group is protected by the publicly known proper protecting groups are also included in the scope of the present invention.

Compounds of formula (I), wherein $X_1$ and $Y_1$ are both hydroxyl groups (not included in the scope of this invention) and $W_1$ and $Z_1$ are hydrogen atoms or hydroxyl groups, can be synthesized by the method with the use of a mercury compound proposed by Bergstrom et al. (J. Org. Chem., 47, 2174 (1982)). Another method is proposed to obtain pyrido-[2,3-d]pyrimidine nucleoside, in which 5-iododeoxyuridine is treated with methyl acrylate in the presence of $Pd(OAc)_2$ and $Ph_3P$ to give a compound, whose hydroxyl groups are protected by acetyl group. Thereafter, triazolidation at its 4-position is performed, followed by the treatment with ammonia to give a deoxycytidine derivative. The obtained derivative is then irradiated with a high pressure mercury lamp in water to give the desired pyrido[2,3-d]pyrimidine nucleoside.

Compounds of formula (I), wherein $R_1$ is halogen, can be obtained by converting the functional groups of the aforementioned pyrimidine nucleoside base. For instance, after the hydroxyl groups of pyrido[2,3-d]pyrimidine nucleoside are protected by acetyl groups, the compound is treated with $POCl_3$ and dimethylformamide in chloroform at 70° C. for 1 hour to obtain the 7-Cl-derivative.

The compound whose $R_1$ is an amino group can be obtained by following the procedure mentioned below. For instance, 5-iododeoxyuridine is allowed to react with acrylonitrile in the presence of $Pd(OAc)_2$ and $Ph_3P$ to give derivative introduced the cyanovinyl group at the 5-position. Thereafter, triazolidation at its 4-position is performed, followed by treatment with ammonia to give a deoxycytidine derivative. Thereafter, an aqueous solution of thus obtained compound is irradiated with a high pressure mercury lamp for 60 minutes to obtain the desired nucleoside.

As described hereinafter, all of these compounds showed fluorescence properties and displayed common characters of the natural pyrimidine bases.

The fluorescent nucleosides thus obtained can be made into nucleotides of this invention by phosphorylation of their 3'-position or 5'-position.

Since thus obtained compounds of formula (I) are fluorescent and capable of forming base pairing with guanine or adenine in the DNA duplex, oligo- or polynucleotides, which have such a nucleoside in their molecules or at their molecular terminals, can be utilized as the fluorescent probes. Also judging from the fact that their base moieties are spatially fitted to each other when the compounds are incorporated in the DNA double helixes, it may be assumed that these compounds have the possibility of enhancing the capability of forming a hydrogen bond between the bases and stacking function.

To speak of formula (II) in this invention, oligo- or polynucleotides in which $X_2$ is

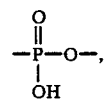

$Y_2$ is —O—, and $W_2$ is a hydrogen atom, are especially desirable.

As for the introduction of the fluorescent nucleoside or nucleotide into DNA oligomers or polymers, there are two methods, being the methods of the organic synthesis and enzymatic synthesis.

The method of the organic synthesis is one in which oligonucleotide which contains fluorescent nucleoside (F) is chemically synthesized. Methods of this type include the phosphotriester solid-phase method developed by Itakura et al. and phosphite-triester method.

(i) The synthesis by the phosphotriester solid-phase method was conducted in accordance with the cycle shown in FIG. 1. In the first step, the dimethoxytrityl group (DMTr group) of 5'-hydroxyl group was removed by use of benzenesulfonic acid (BSA) and in the second step, the dimer block was condensed with mesitylenesulfonic acid nitrotriazole (MSNT) to lengthen the chain of the oligomer containing F carried by a solid-support S . To prevent the formation of oligomer of undesired sequences, 5'-hydroxyl groups unreacted in the condensation reaction were capped with acetic anhydride (Ac₂O) in the presence of 4-dimethylaminopyridine (DMAP).

By repeating the aforementioned cycle, the desired oligomer was synthesized. The cutting off of oligonucleotide from the polymer supporter and the deprotection of the protecting group of the inter nucleotide bonds were carried out by the treatment with aqueous ammonia at room temperature.

Then an acyl protecting group was eliminated from the base moiety by heat-treatment in aqueous ammonia. The product was purified by reverse-phase column chromatography on silica gel, and the desired fractions were taken and DMTr group at the 5'-terminal was removed. Thereafter, the product was further purified by high performance liquid chromatography.

Figure 6:
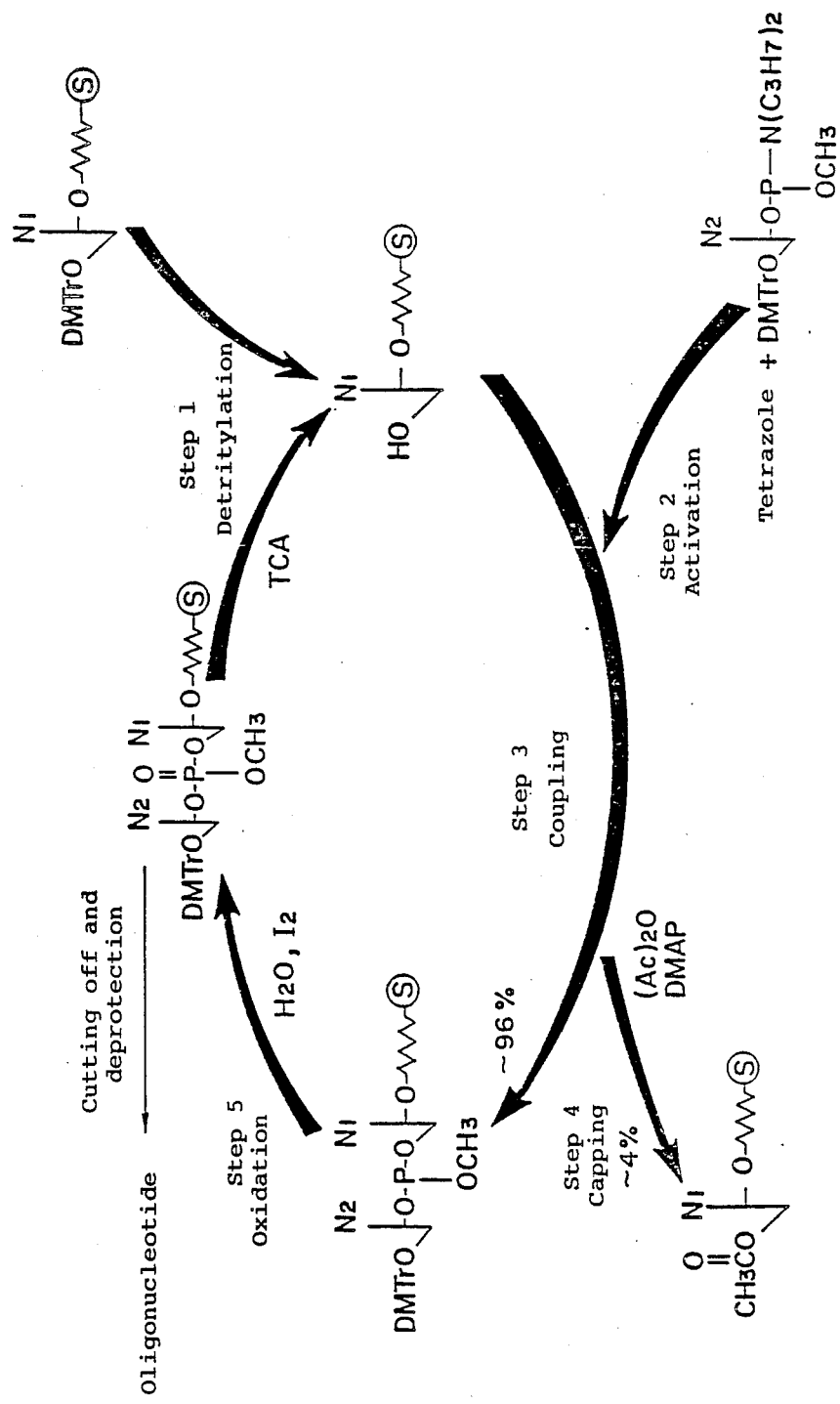
FIG. 6 shows a procedure of synthesis of oligonucleotide by the phosphite-triester method.

(ii) The synthesis by the phosphite-triester method was carried out in accordance with the cycle shown in FIG. 6. In the first step, the dimethoxytrityl group (DMTr) of 5'-hydroxyl group was removed by use of trichloroacetic acid (TCA), and in the second step, nucleoside-3'-phosphoamidite was activated with the use of tetrazole. In the third step, the activated nucleoside-3'-phosphoamidite was coupled with the 5'-hydroxyl group of the supported nucleotide chain. The unreacted 5'-hydroxyl groups were subjected to capping with acetic anhydride in the presence of 4-dimethylaminopyridine (DMAP). In the fifth step, trivalent phosphorus was oxidised to pentavalent by the use of iodine. The desired oligomer was synthesized by repeating these cycle. After the removal of the protecting group from phosphoric acid was carried out with the use of thiophenol, oligonucleotide was cut off from the polymer supporter in aqueous ammonia. Thereafter, the product was purified according to the generally approved method.

As the method of introducing fluorescent nucleoside or nucleotide into the DNA oligomers or polymers according to enzymatic synthesis, there are two ways generally practiced as mentioned below:

(i) Nick translation by use of DNA polymerase (see Rigby, P. W. et al., J. Mol. Biol., 113, 237 (1977)).

(ii) 3'-Terminal addition reaction by use of terminal deoxynucleotidyl transferase (see F. J. Bollum, The Enzymes, (P. D. Boyer, ed.), 3rd Ed. Vol. 10, pp. 145-171, Academic Press, New York, N.Y. (1974)).

In the case where any one of these enzymes are used, nucleoside 5'-triphosphate is necessary as the substrate. Fluorescent nucleoside 5'-monophosphate can be synthesized by the method proposed by Yoshikawa et al. (Tetrahedron Lett., 5065 (1976). Also, the synthesis of 5'-triphosphate from 5'-monophosphate via the corresponding imidazolide through the reaction with diphosphate can be achieved according to the method of Otto et al. (J. Am. Chem., Soc., 87, 1785-1788 (1065)).

When Nick translation is conducted with the use of thus synthesized 5'-triphosphate as the substrate and DNA polymerase, a fluorescence-labeled oligomer or polymer, which has a fluorescent nucleotide introduced thereinto, can be prepared instead of cytidine. The use of terminal deoxynucleotidyl transferase in this case makes it possible to add a fluorescent nucleotide polymer to the 3'-terminal.

The present invention is described in detail by the following referential examples and examples.

REFERENTIAL EXAMPLE 1

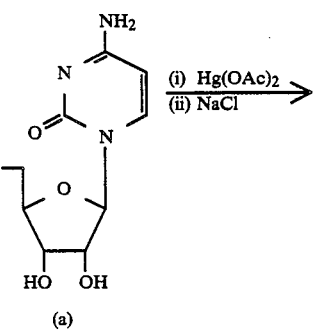

(a)

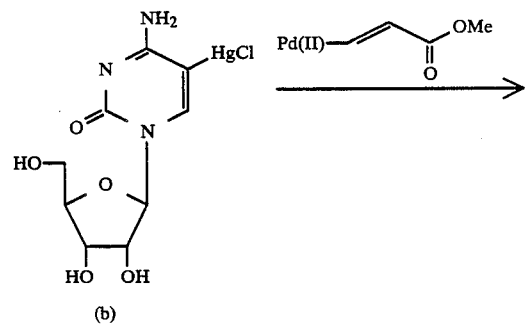

(b)

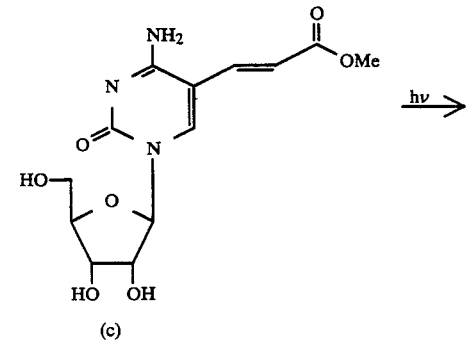

(c)

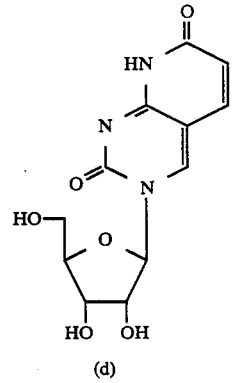

(d)

(1) An aqueous solution was prepared by dissolving 14.7 g of cytidine (a) in 200 ml of distilled water and 21.5 g of mercuric acetate was added thereto. The mixture was made to undergo an reaction at 70° C. for 6 hours. After the reaction mixture was cooled off, 20 ml of an aqueous solution of 6.5 M sodium chloride was added and the reaction was conducted at room temperature for 1 hour. The resulting white precipitate was collected by filtration, washed once with 25 ml of 0.1 M sodium chloride, twice with 100 ml of distilled water, twice with 100 ml of ethanol, and twice with 100 ml of diethyl ether, and was dried under reduced pressure to obtain 27 g of 5-fluoromercuric cytidine (b).

(2) A suspension of 19.1 g of 5-chloromercuriccytidine (b) in 150 ml of methanol was prepared and then 210 ml of a methanol solution of 0.1 M lithium palladium chloride ($Li_2PdCl_4$), 40 ml of methyl acrylate, and 4.12 g of cupric chloride were added to above suspension and the mixture was stirred at room temperature for 14 hours. The palladium precipitate was removed by filtration and hydrogen sulfide was bubbled into the filtrate and the formed precipitate was removed by Celite filtration. The filtrate was neutralized with a saturated sodium bicarbonate solution and evaporated to dryness under reduced pressure. The residue was recrystallized from aqueous solution to give 4.62 g of (E)-5-(2-methoxycarbonyl ethenyl) cytidine (c).

(3) A solution was prepared by dissolving 590 mg of (E)-5-(2-methoxycarbonylethenyl) cytidine (c) and irradiated with a high pressure mercury lamp (Ushio UM 102) for 30 minutes.

The reaction solution was evaporated to dryness under reduced pressure and the residue was recrystallized from water to obtain 508 mg of 3-β-D-ribofuranosyl-2,7-dioxopyrido[2,3-d] pyrimidine (d). Its physical properties were as follows:

m.p. 240° C.
UV $\epsilon_{max}^{H2O}$ 330nm ($\epsilon$=15,800),
250nm ($\epsilon$=15,000)
Mass m/e 295 (M+)
NMR (DMSO-$d_6$-$D_2O$)
δ+9.05 (s, 1H), 7.58 (d, 1H, J=9 Hz), 6.19 (d, 1H, J=9 Hz), 5.81 (s, 1H), 4.02 (m, 3H), 3.70 (m, 2H)

| Elementary analysis values calculated for $C_{12}H_{13}O_6N_3$; | | | |
|---|---|---|---|
| | C | H | N |
| Calculated (%) | 48.82 | 4.43 | 14.23 |
| Found (%) | 48.61 | 4.37 | 14.01 |

REFERENTIAL EXAMPLE 2

By using 2'-deoxycytidine as a starting material in the place of cytidine, 3-β-D-2'-deoxyribofuranosyl-2,7-dioxopyrido[2,3-d]pyrimidine was obtained according to the same method as Referential Example 1.

REFERENTIAL EXAMPLE 3

By use of arabinosylcytosine as a starting material in the place of cytidine, 3-β-D-arabinofuranosyl-2,7-dioxopyrido[2,3-d]pyrimidine was obtained according to the same method as Referential Example 1.

REFERENTIAL EXAMPLE 4

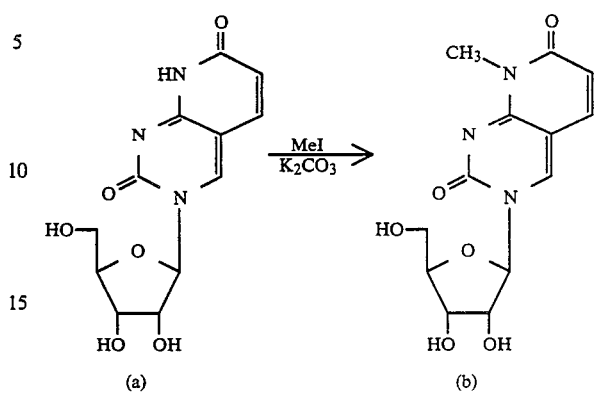

A solution of 295 mg of 3-β-D-ribofuranosyl-2,7-dioxopyrido[2,3-d]pyrimidine (a) in 10 ml of absolute dimethylformamide was prepared, and 0.1 ml of methyl iodide and 0.21 g of potassium carbonate were added thereto. The mixture was made to undergo the reaction at room temperature for 12 hours. After the removal of potassium carbonate by filtration, the filtrate was neutralized with acetic acid and condensed to dryness under reduced pressure. The residue was recrystallized from water to obtain 279 mg of 3-β-D-ribofuranosyl-2,7-dioxo-8-methylpyrido [2,3-d]pyrimidine (b). Its physical properties were as follows:

m.p. 263°~265° C.
UV $\lambda_{max}^{H2O}$ 330nm ($\epsilon$=15,300)
253nm ($\epsilon$=15,400).
Mass m/e 309 (M+).
NMR (DMSO-$d_6$-$D_2O$).
δ+9.06 (s, 1H), 7.57 (d, 1H, J=9.5 Hz), 6.31 (d, 1H, J=9.5 Hz), 5.79 (s, 1H).

| Elementary analysis values calculated for $C_{13}H_{15}O_6N_3$; | | | |
|---|---|---|---|
| | C | H | N |
| Calculated (%) | 50.49 | 4.89 | 13.59 |
| Found (%) | 50.49 | 4.83 | 13.55 |

REFERENTIAL EXAMPLES 5

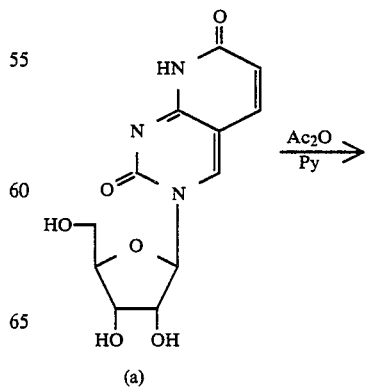

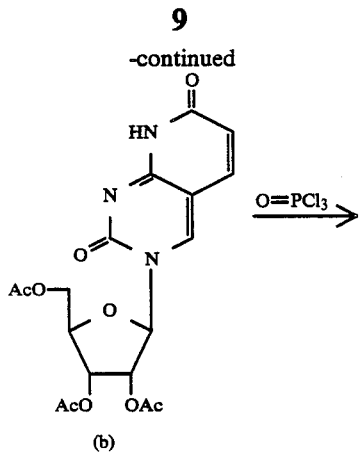

(b)

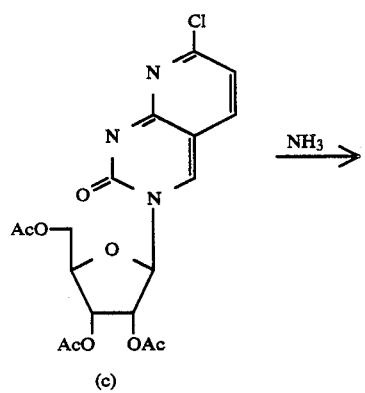

(c)

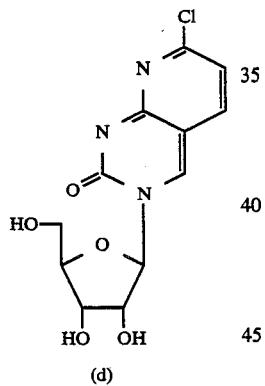

(d)

(1) A solution of 2.01 g of 3-β-D-ribofuranosyl-2,7-dioxopyrido[2,3-d]pyrimidine (a) in 50 ml of anhydrous pyridine was prepared and 8 ml of acetic anhydride was added thereto. The mixture was allowed to go through the reaction at room temperature for 12 hours. 10 ml of methanol was added to the reaction mixture on the ice bath and the solvent was distilled away under reduced pressure. The resulting residue was recrystallized in an ethanol-water system to obtain 2.40 g of 2',3', 5'-tri-O-acetyl-3-β-D-ribofuranosyl-2,7-dioxopyrido[2,3-d]pyrimidine (b).

(2) A mixture comprising 0.3 ml of phosphorus oxychloride, 20 ml of anhydrous chloroform, and further 0.2 ml of dimethylformamide added together in this order was made to undergo a reaction at room temperature for 10 minutes. Thereafter, 630 mg of 2',3',5'-tri-O-acetyl-3-β-D-ribofuranosyl-2,7-dioxopyrido[2,3-d]pyrimidine (b) was added to it and the reaction was carried on at 70° C. for 2 hours. The reaction mixture was concentrated under reduced pressure, extracted with a chloroform-water system, and the chloroform layer was dried with anhydrous sodium sulfate. After the removal of chloroform by distillation at reduced pressure, the reaction product was purified by column chromatography on silica gel to obtain 408 mg of 2',3',5'-tri-O-acetyl-3-β-D-ribofuranosyl-2-oxo-7-chloropyrido[2,3-d]pyrimidine (c).

(3) 44 mg of 2',3',5'-tri-O-acetyl-3-β-D-ribofuranosyl-2-oxo-7-chloropyrido[2,3-d]pyrimidine (c) was dissolved in 1 ml of methylene chloride and 10 ml of ammonia saturated methanol was added thereto. The mixture was made to undergo a reaction at room temperature for 12 hours. Thereafter, the reaction mixture was concentrated at reduced pressure and the residue was recrystallized in an ethanol-water system to give 26 mg of 3-β-D-ribofuranosyl-2-oxo-7-chloropyrido[2,3-d]pyrimidine (d). Its physical properties were as follows.

m.p. 189°~190° C.

UV $\lambda_{max}^{H2O}$ 293nm($\epsilon$=8,400).

Mass m/e 314 (M+).

NMR (DMSO-$d_6$).

δ+10.58 (br s, 1H), 7.81 (d, 1H, J=8.1 Hz), 7.08 (d, 1H, J=8.1 Hz), 6.07 (s, 1H), 5.50 (s, 1H).

| | Elementary analysis values calculated for $C_{12}H_{12}O_5N_3Cl.H_2O$: | | | |
|---|---|---|---|---|
| | C | H | N | Cl |
| Calculated (%) | 43.33 | 4.25 | 12.67 | 10.70 |
| Found (%) | 43.66 | 4.13 | 12.72 | 10.74 |

REFERENTIAL EXAMPLE 6

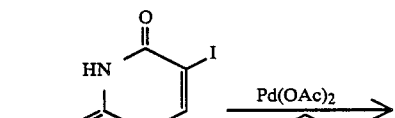

(a)

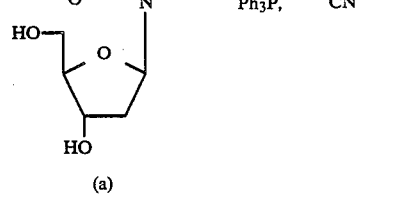

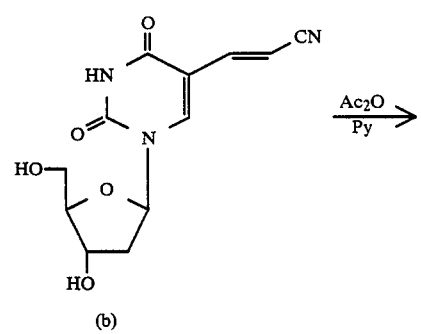

(b)

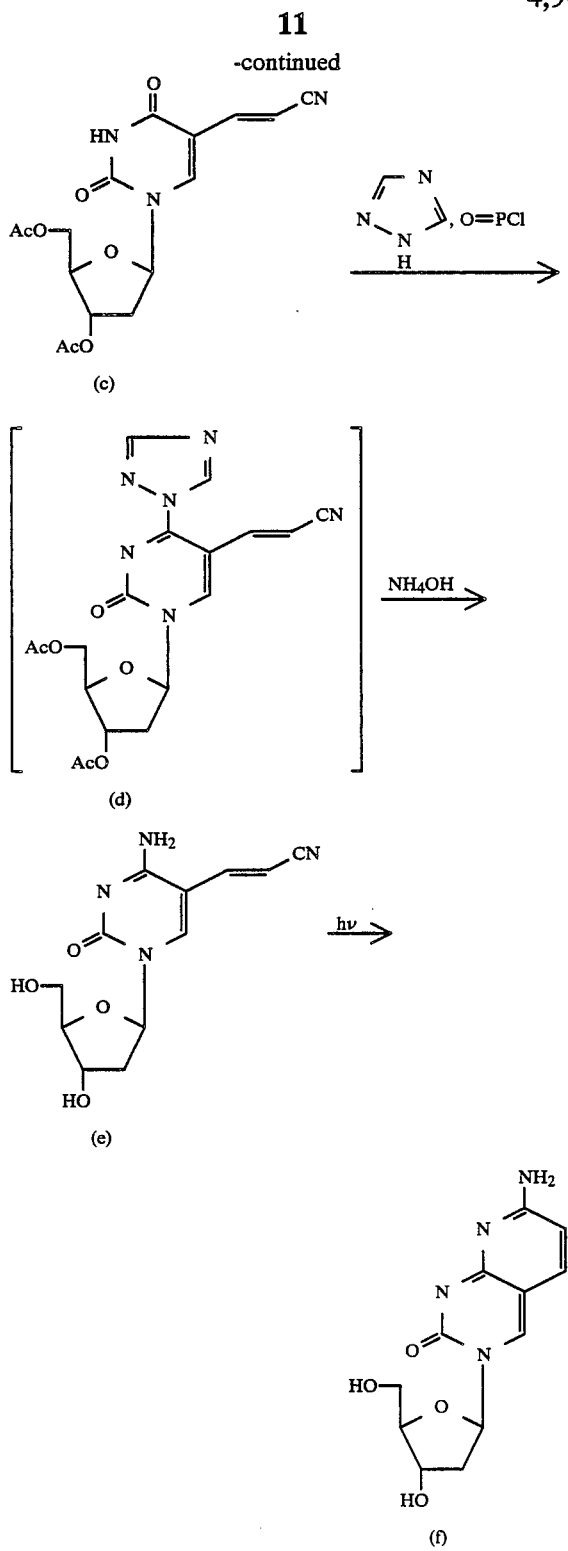

was refined by column chromatography on silica gel to obtain 159 mg of (E)-5-(2-cyanoethenyl)deoxyuridine (b).

(2) A solution of 140 mg of (E)-5-(2-cyanoethenyl) deoxyuridine (b) in 5 ml of anhydrous pyridine was prepared and 1 ml of acetic anhydride was added to the solution. The reaction was made to go on at room temperature for 12 hours. While cooling the mixture, 10 ml of methanol was added and the reaction was continued for 10 minutes. After the solvent was distilled away at reduced pressure, the residue was recrystallized in ethanol-water system to obtain 168 mg of 3',5'-di-O-acetyl-(E)-5-(2-cyanoethenyl)deoxyuridine (c).

(3) 2.00 g of 3',5'-di-O-acetyl-(E)-5-(2-cyanoethenyl)-deoxyuridine (c).

(3) 2.00 g of 3', 5'-di-O-acetyl-(E)-5-(2-cyano-ethenyl) deoxyuridine (c) was dissolved in 20 ml of absolute acetonitrile, to which 9.2 ml of triethylamine, 1.12 ml of phosphorus oxychloride, and further 50 ml of 1.3 M triazole acetonitrile solution were added. The mixture was allowed to undergo a reaction at room temperature for 90 minutes. Water was added to the reaction mixture and it was left standing for 10 minutes. The reaction mixture was evaporated to dryness at reduced pressure and the residue was extracted in water-chloroform system. After the chloroform layer was dried with anhydrous sodium sulfate, chloroform was distilled away at reduced pressure. The residue was dissolved in 20 ml of dioxane, and after addition of aqueous ammonia, the mixture was left standing at room temperature for 12 hours. It was concentrated to dryness under reduced pressure. The residue was purified by C-18 reverse phase column chromatography on silica gel (20% acetone/water) to give 1.28 g of (E)-5-(2-cyanoethenyl) deoxyuridine (e).

(4) A solution prepared by dissolving 250 mg of (E)-5-(2-cyanoethenyl)deoxyuridine (e) in 500 ml of distilled water was irradiated with a high pressure mercury lamp for 60 minutes. The reaction mixture was concentrated under reduced pressure and the residue was purified by column chromatography on silica gel and was recrystallized from water to obtain 159 mg of 3-$\beta$-D-deoxyribofuranosyl-2-oxo-7-aminopyrido [2,3-d]pyrimidine (f). Its physical properties were as follows.

m.p. 220° C. (colored).

UV (neutral) 252 , 308nm (acidic, pH 4.0) 257, 350, 363nm.

NMR (DMSO-$d_6$) (neutral) $\delta$+7.28 (d, J=8.3 Hz), 6.18 (s, −NH$_2$) 6.07 (d, J=8.3 Hz), 5.88 (d, 1H, H-1'), 5.85 (s, 1H, H-4)

(DMSO-$d_6$-CF$_3$COOH-D$_2$O) $\delta$+8.87 (s, 1H, H-4'), 7.91 (d, 1H, J=9.3 Hz), 6.69 (d, 1H, J=9.3 Hz) 6.10 (t, 1H, H-1').

| Elementary analysis values calculated from $C_{12}H_{14}O_4N_4$: | | |
|---|---|---|
| C | H | N |
| Calulated (%) 51.79 | 5.07 | 20.13 |
| Found (%) 51.64 | 5.10 | 20.05 |

(1) A solution was prepared by dissolving 460 mg of 5-iododeoxyuridine (a) in 20 ml of absolute dioxane, to which 22 mg of palladium acetate, 34 mg of triphenylphosphine, 0.3 ml of triethylamine, and 0.13 ml of acrylonitrile were added and the mixture was made to undergo a reaction at 100° C. for 12 hours. After the removal of the precipitate by filtration, a hydrogen sulfide gas bubbled into the filtrate and the resulting precipitate was removed by filtration with Calite. The filtrate was concentrated under reduced pressure and the residue

REFERENTIAL EXAMPLE 7

By using methyl acrylate instead of acrylonitrile, 3-$\beta$-D-ribofuranosyl-2,7-dioxopyrido [2,3-d]pyrimidine was obtained according to Referential Example 1. The physical properties of this product perfectly coincided with those of the product synthesized in Referential Example 1.

The fluorescent characteristics of various pyrido pyrimidine nucleoside derivatives synthesized by the aforementioned methods are shown in Table 1. The characteristics of 1,N$^6$-ethenoadenosine are also shown for the reference compound (relative intensity is based on ethenoadenosine). F means 3-β-D-ribofuranosyl-2,7-dioxopyrido[2,3-d]pyrimidine; dF means its 2'deoxy derivative; and 8-Me, 7-Cl, and 7-NH$_2$ respectively mean that the 8-and 7-positions are substituted by a methyl group, chloro group, and amino group.

TABLE 1

| Derivative | λmax (nm) | λex (nm) | λem (nm) | Relative fluoroescence intensity |
|---|---|---|---|---|
| F | 250, 330 | 330 | 380 | 17.3 |
| dF | 250, 330 | 330 | 380 | 17.4 |
| 8-Me-F | 253, 330 | 330 | 385 | 10.4 |
| 7-Cl-F | 293 | 330 | 385 | 2.9 |
| 7-NH$_2$-F | 252, 308 | 308 | 356 | 8.7 |
| 7-NH$_2$-F* | 257, 350, 363 | 350 | 396 | 25.3 |
| Ethenoadenosine | 265, 275 | 300 | 410 | 1.0 |

Fluoroescent spectra were measured at pH 7.0
(* measured at pH 4.0).

Table 1 makes it apparent that all the derivatives show a more intensive fluorescence than ethenoadenosine; that, when the 8- and 7-positions are substituted, the fluorescence intensity decreases; and that the one, whose 7-position is the amino group, comes to have strong fluorescence under acid conditions.

Figure 2:
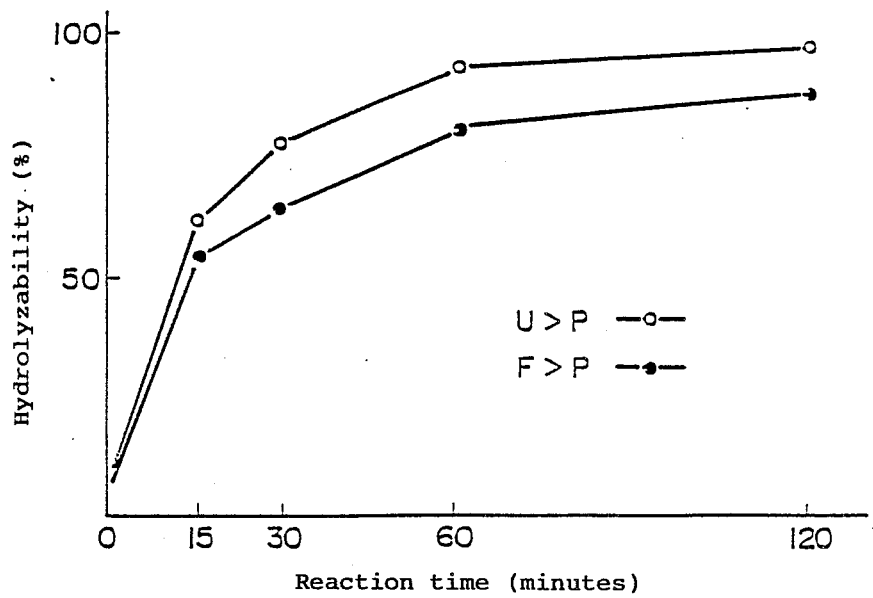
FIG. 2 shows the hydrolytic reaction in which the pyridopyrimidine nucleotide was digested by the RNase A.

It was then studied whether 3-β-D-ribofuranosyl-2,7-dioxopyrido[2,3-d]pyrimidine (F) would be recognized as well as natural pyrimidine nucleotide. A 2',3'-O-cyclic phosphate derivative was synthesized by subjecting the compound F to the heat-treatment with the use of polyphosphoric acid and tributylamine in dimethylformamide according to the method proposed by Ueda et al. (Chem. Pharm. Bull., 18, 2303–2308 (1970)). Thus obtained cyclic phosphate derivatives and RNase A which may digest specific to pyrimidine nucleotide were incubated at 37° C. to inspect its hydrolyzability. As the comparison, uridinenucleoside (U) was also subjected to the same treatment. The result is shown in FIG. 2. FIG. 2 apparently shows that the compound F is as highly hydrolyzable as uridine derivative:

EXAMPLE 1

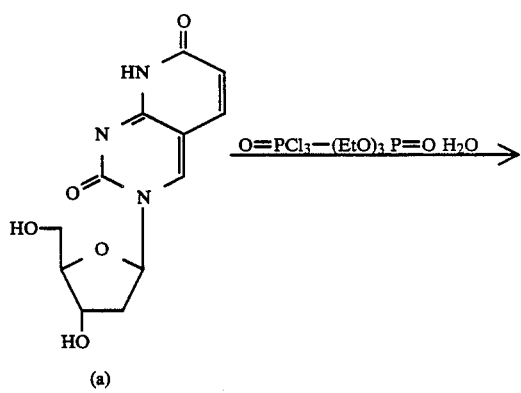

(a)

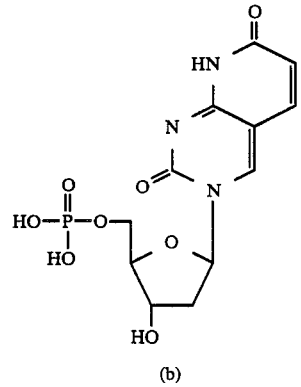

(b)

A solution of 560 mg of 3-β-D deoxyribofuranosyl-2,7-dioxopyrido[2,3-d]pyrimidine (a) in 5 ml of triethylphosphate was cooled to 0° C. and 613 mg of phosphorus oxychloride was added thereto. After the mixture was made to undergo a reaction for 6 hours, 1 g of ice was added to effect a hydrolysis. The reaction mixture was concentrated at reduced pressure and the resulting residue was dissolved in 1 ml of distilled water. The purification of the product was carried out by column chromatography on DEAE-Sephadex A-25 (HCO$_3$-form) by use of a linear gradient of triethylammonium bicarbonate to obtain 575 mg of 3-(5'-O-phosphoryl-β-D-2'-deoxyribofuranosyl)-2,7-dioxopyrido[2,3-d]pyrimidine (b).

EXAMPLE 2

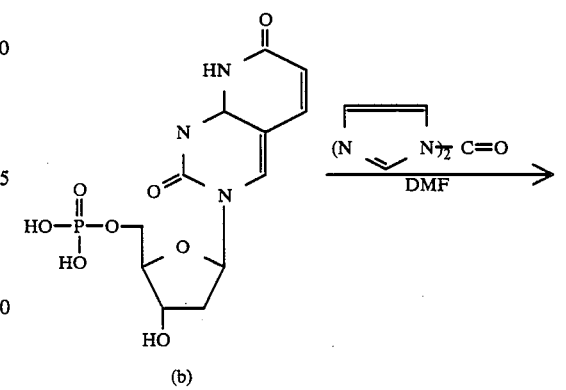

(b)

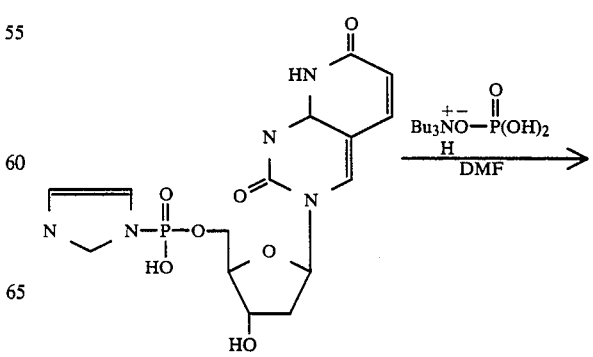

-continued

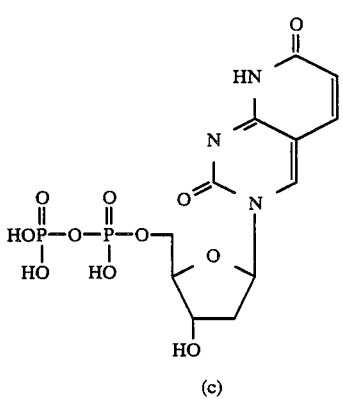

(c)

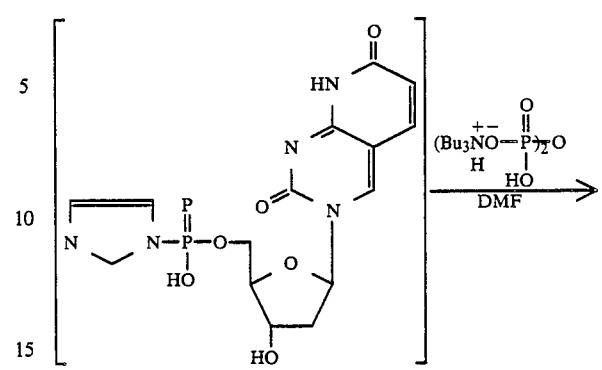

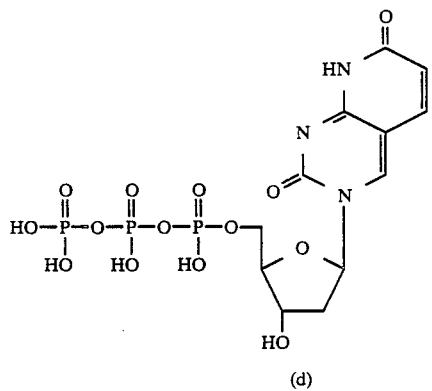

(d)

A solution was prepared by dissolving 88 mg of 3-(5'-O-phosphoryl-β-D-deoxyuribofuranosyl)-2,7-dioxopyrido[2,3-d]pyrimidine (b) in 5 ml of anhydrous dimethylformamide, and 400 mg of carbonyl diimidazole was added to the solution. The mixture was made to undergo a reaction at room temperature for 1 hour. Thereafter, the reaction mixture was poured into 20 ml of 1% sodium iodide/acetone and the resulting precipitate was separated by filtration, washed with acetone, and dried at reduced pressure. The precipitate was dissolved in 5 ml of anhydrous dimethylformamide, and 2 g of mono-tri-n-butyl ammonium phosphate was added to the solution, and the mixture was allowed to undergo a reaction at room temperature for 24 hours. After the reaction mixture was concentrated under reduced pressure, the residue was dissolved in 3 ml of distilled water and purified with the use of DEAE-Sephadex A-25 (HCO$_3$-form) by means of a linear gradient of triethylammonium bicarbonate to obtain 53 mg of 3-(5'-O-diphosphoryl-β-D-deoxyuribofuranosyl)-2,7-dioxopyrido[2,3-d]pyrimidine (c).

EXAMPLE 3

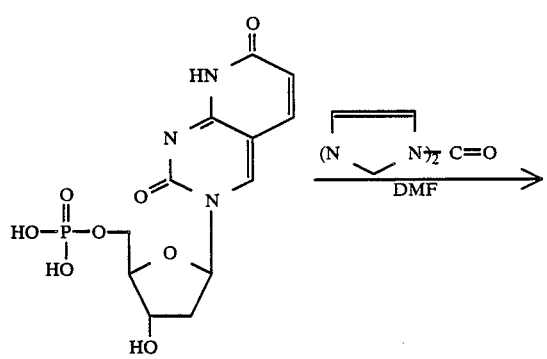

3-(5'-O-triphosphoryl-β-D-deoxyribofuranosyl)2,7-dioxopyrido[2,3-d]pyrimidine (d) was obtained according to the same procedures as taken in Example 2, wherein di-tri-n-butyl ammonium diphosphate was used in the place of mono-tri-n-butyl ammonium phosphate.

EXAMPLE 4

A synthesis of the dodecamers containing a fluorescent pyrimidine nucleotide of this invention was carried out by the phosphotriester solid-phase method (see FIG. 1) as described below. The solid-phase support was made to effect a support with the use of 1% cross-linked polystyrene resin by bonding a 3'-hydroxyl group of the 3'-terminal cytidine and the resin with succinic acid ester. The synthesis was effected by the dimer block-condensation according to the cycle shown in FIG. 1.

Step 1 (Detritylation reaction)

Detritylation was effected with the use of the resin corresponding to 5 μ mol of nucleoside by repeating a 1-minute treatment with a chloroform solution of 2% benzenesulfonic acid (BSA) twice.

Step 2 (Condensation reaction)

A solution was prepared by dissolving 20 μ mol of dimer in 200-300 μl of pyridine and 70 μ mol of mesitylenesulfonyl introtriazole (MSNT) was added thereto as the condensing agent. The mixture was made to undergo a reaction at 40° C. for 20 minutes.

Step 3 (Capping reaction)(Reaction for protection of the unreacted product)

A mixture of 0.2 ml of acetic anhydride (Ac$_2$O) and 1.8 ml of a pyridine solution of 0.1 M 4-dimethylaminopyridine (DMAP) (made up freshly at the time of use) was made to undergo a reaction.

The procedures (Steps 1 to 3) were repeated five times to synthesize dodecamers.

The dodecamers (dGGGAAFTTTCCC...F being a fluorescent nucleoside) thus synthesized were deprotected and purified by following the procedures described below.

(i) After the addition of 16 ml of concentrated aqueous ammonia and 4 ml of pyridine to the obtained dodecamers and the mixture was allowed to undergo a reaction for 24 hours at room temperature.

(ii) The temperature was then raised to 50° C. and the reaction was carried on for 4 hours.

(iii) The reaction product was purified (acetonitrile gradient : 10%–35%) by reverse-phase column chromatography on silica gel (C18 column: Waters, 35–100 μm).

(iv) The purified product was dissolved in 80% acetic acid and worked up to room temperature for 20 minutes to remove the dimethoxytrityl group from the 5'-terminal (v) Thus treated product was purified by reverse-phase high pressure liquid chromatography (TSK-410AK: Toyo Soda).

(vi) The product was further purified by ion-exchange high pressure liquid chromatography (on a column of TSK gel IEX 540K : Toyo Soda) to obtain a single peak.

The synthesis of 5 kinds of self-complementary dodecamers as mentioned below was carried out according to the aforementioned method.

| 5' | dGGGAA | CG | TTCCC | 3' |
|---|---|---|---|---|
| 3' | CCCTT | GC | AAGGGd | 5' |
| 5' | dGGGAA | FT | TTCCC | 3' |
| 3' | CCCTT | TF | AAGGGd | 5' |
| 5' | dGGGAA | FC | TTCCC | 3' |
| 3' | CCCTT | CF | AAGGGd | 5' |
| 5' | dGGGAA | FA | TTCCC | 3' |
| 3' | CCCTT | AF | AAGGGd | 5' |
| 5' | dGGGAA | FG | TTCCC | 3' |
| 3' | CCCTT | GF | AAGGGd | 5' |

In the study of the UV spectra of the dodecomers, the existence of fluorescent nucleotide was confirmed from the absorbance at 343 nm.

(2) Absorption (260 nm) versus temperature was studied at to the respective dodecamers to calculate the Tm. The results are shown in Table 2, FIGS. 3 and 4 (measuring conditions: concentration 0.75 $A_{260}$, solvent 0.1 M NaCl and 0.01 M sodium cacodylate). It is apparent that dodecamer No. 2 and 3 had no transition points (see FIG. 4) and that they had no self complementary double-strand structure formed at the temperature through the measurement.

It was possible to calculate the Tm for all the dodecamer No. 1, 4, and 5 (see FIG. 3), and the interesting results were obtained. 1 It may be observed from the difference in Tm between No. 1 and No. 5 that the exchange from C into F of the dodecamer causes the increase of Tm (50.5° C. to 58.4° C.) and so brings about the effect of stabilizing the complementary base pairing. More particularly, the exchange from C to F not only maintains of the dodecamer the hydrogen bond with G but also stabilizes the base pairing. This fact may most possibly lead to an assumption that much stronger hybridization may be expected in case F is introduced into the DNA probe, thus resulted in the improvement of sensitivity. 2 It has been found from the difference in Tm between No. 4 and No. 5 that F forms the hydrogen bonding not only with G but also with A, though the bond with A is weaker than with G.

TABLE 2

| No. | dodecamer | λmax (nm) | Tm (°C.) | Relative fluorescence intensity |
|---|---|---|---|---|
| | dF | 330, 250 | | 100 |
| 1. | dGGGAACGTTCCC | 257 | 50.5 | 0 |
| 2. | dGGGAAFTTTCCC | 333, 258 | | 25.3 |
| 3. | dGGGAAFCTTCC | 333, 258 | | 21.0 |
| 4. | dGGGAAFATTCCC | 341, 257 | 39.4 | 1.7 |
| 5. | dGGGAAFGTTCCC | 338, 255 | 58.4 | <1.0 |

Figure 5:
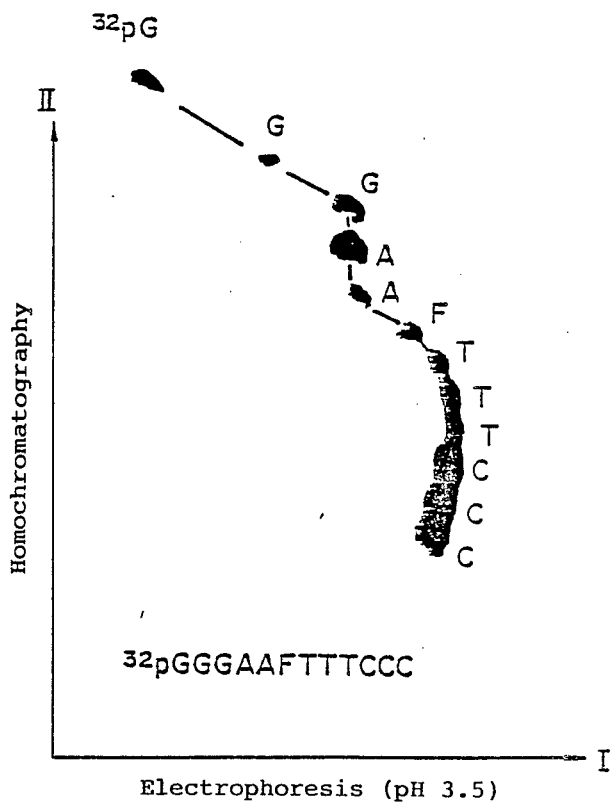
FIG. 5 shows the finger-print profile of oligonucleotide of this invention obtained by mobility shift analysis.

(3) The 5'-terminal of dodecamer No. 2 was radioisotope-labeled ($^{32}$P) and was then subjected to limited hydrolysis with snake venom phosphodiesterase and its finger print was obtained with two-dimensional homochromatography to give the result as shown in FIG. 5. From the result shown in FIG. 5, it has been confirmed that the pyrimidine nucleotide can work as a substrate as well as the natural nucleotides and that its nucleotide sequence is confirmed.

EXAMPLE 5

A pentadecamer which contains the fluorescent pyrimidine nucleotide of this invention was synthesized by the following method.

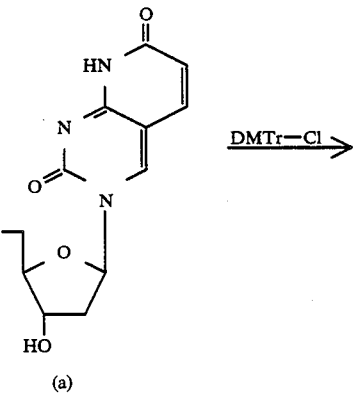

(a)

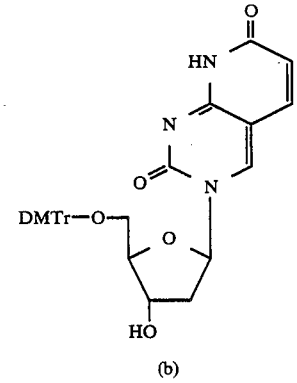

(b)

A suspension of 279 mg of 3-β-D-dioxyribofuranosyl-2,7-dioxopyrido[2,3-d]pyrimidine (a) in 15 ml of pyridine was prepared and then 0.194 ml of triethylamine, 6 mg of dimethylaminopyridine DMAP), and 407 mg of 4,4'-dimethoxy trityl chloride (DMTr—Cl) were added thereto. After the mixture was made to undergo a reaction at room temperature for 5 hours, 15 ml of water was added, and extracted with diethyl ether. The residual solution as distilled away at reduced pressure and the reaction product was purified by silica gel column chromatography to obtain 490 mg of 3-(5'-dimethoxy trityl-β-D-deoxyribofuranosyl)2,7-dioxopyrido[2,3-d]pyrimidine (b).

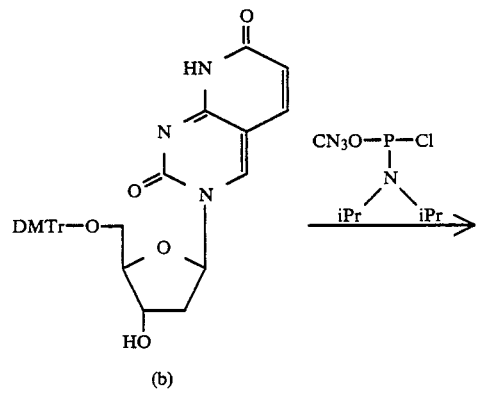

(b)

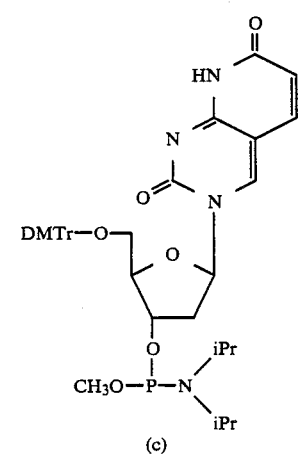

(c)

490 mg of 3-(5'-O-dimethoxy trityl-β-D-deoxyribofuranosyl)-2,7-dioxopyrido[2,3-d]pyrimidine (b) was dissolved in 5 ml of CH₂Cl₂ and 0.585 ml of diisopropyl ethylamine was added to the solution. After the addition of 0.244 ml of chloro-N,N-diisopropylaminomethoxyphosphine to the solution drop by drop slowly, the mixture was allowed to stand for 15 minutes, and 0.2 ml of methanol was further added thereto. The mixture was then extracted with 30 ml of ethyl acetate and 1.5 ml of triethylamine. The solvent was removed by distillation at reduced pressure and the residual product was purified by silica gel column chromatography to give 330 mg of 3-(5'-O-dimethoxytirtyl-3'-O-diisopropylamino methoxyphosphinyl-β-D-deoxyribofuranosyl)-2,7-dioxopyrido[2,3-d]pyrimidine (c).

(3) By using 3-(5'-O-dimethoxytrityl-3'-0-diisopropylamino methoxyphosphinyl-β-D-deoxyribofuranosyl)-2,7-dioxopyrido[2,3-d]pyrimidine (c) as the starting material for DNA synthesizer (Applied Biosystem Inc.), the pentadecamer which contained fluorescent pyrimidine nucleotide of this invention was synthesized by the phosphite-triester method (see FIG. 6).

Thus synthesized pentadecamer was deprotected and purified by following the procedures described below. The pentadecamer was dissolved in concentrated aqueous ammonia, was left standing overnight at 55° C., had ammonia removed by distillation at reduced pressure, filtrated by Sephadex G-50, concentrated, and precipitated with ethanol. After dissolving the precipitate in formamide, the solution was subjected to the electrophoresis with 7 M urea and 20% polyacrylamide gel to cut off the desired bands which contained pentadecamer, and extracted with 0.5 M ammonium acetate, 1% sodium dodecyl sulfate (SDS) and 1 mM EDTA, and concentrated. The concentrate was precipitated with ethanol to obtain 3 types of pentadecamers as shown below.

|       |    |                  |    |
|-------|----|------------------|----|
| (i)   | 5' | dAGAGCGTCGACCGAT | 3' |
| (ii)  | 5' | dAGAGCGTFGACCGAT | 3' |
| (iii) | 5' | dAGAGCGTFGAFCGAT | 3' |

Pentadecamer (i) is a sequence which involves Sal I recognizing site in pBR 322 (PBR 322 base numbers: (645–659)) and, in the same sequences, (ii) exchange one cytidine (C) into fluorescent pyridine nucleotide (F) of the present invention and (iii) exchange two cytidines likewise. In the UV spectra of pentadecamers (ii) and (iii), the existence of fluorescent nucleotides had been confirmed from the absorbance at 330 nm.

EXAMPLE 6

Labeling of 5'-terminal of pentadecamers

The mixture of 10 μl of an aqueous solution of pentadecamer (20p mol), 3 μl of kinase buffer (0.5 M Tris-HCl, pH 7.6, 0.1 M MgCl₂, 50 mM dithio threitol, 1 mM spermidine, and 1 mM EDTA), ( and 5 μl of [r-³²P]-ATP (50 μ Cl) were added to make up a total volume of 29 μl with water. After the mixture is vortexed, 1 μl (2.5u) of T4 polynucleotide kinase was added thereto and made to undergo a reaction at 37° C. for 30 minutes. The enzyme reaction was terminated by adding 1.2 μl of 0.25 M EDTA, and 50 μl of water and 3 μl of denatured salmon sperme DNA (10 mg/ml) were added. Thereafter extracted with phenol, the water layer was subjected to Sephadex G-50F Column collect fractions of pentadecamer. Then the collected pentadecamer was precipitated with ethanol and the precipitate was dissolved in water. The solution was kept in cold storage at −20° C. until it was used as DNA probe in hybridization reaction with pBR 322.

EXAMPLE 7

Hybridization of the 5'-terminal labeled pentadecamer with pBR 322

A mixture comprising pBR 322 and 10 mM Tris-HCl pH 8.0, 1 mM EDTA in a ratio of 25 μg/100 μl was heated at 100° C. for 10 minutes, and then rapidly cooled at 0° C. for 1 minute. Thereafter, a series of dilutions were prepared by use of 20 mM Tris—HCl pH 7.4, 1 mM EDTA and the solutions were used for blotting upon a nitrocellulose membrane in such a way as to put 0.5 μg, 0.25 μg, 0.125 μg, 0.062 μg, 0.031 μg, and 0.016 μg of pBR 322 per spot. The blotted nitrocellulose membrane was treated with 1.5 M NaCl, 0.5 M NaCl—HCl for 3 minutes, then with 1.5 M NaCl, 0.5 M Tris—HCl pH 7.2, 1 mM EDTA for 3 minutes. After having been dried, the membrane was heated at 80° C. for 2 hours in a vacuum oven.

The treated nitrocellulose membrane filter was subjected to prehybridization in 6×SSC (0.9 M NaCl, 0.09

M sodium citrate), 0.5% SDS, denatured salmon sperm DNA 20 μg/ml, and Denhardt's solution (0.1% bovine serum albumin, 0.1% Ficoll, 0.1% polyvinyl pyrrolidone) at 55° C. for 3 hours. Thereafter, the hybridization was carried out by adding the DNA probes (i), (ii), and (iii) prepared in Example 6 to 6×SSC, 0.5% SDS, denatured salmon sperm DNA 20 μ/ml, and Denhardt's solution to make a concentration of $10^6$ cpm/ml at 55° C. for 18 hours. The nitrocellulose filter was then washed with 2×SSC (0.3 M NaCl, 0.03 M sodium citrate) two times and with 2×SSC, 0.1% SDS once at 55° C., dried, and subjected to autoradiography. Then the nitrocellulose filter was washed twice with 2×SSC and once with 2×SSC, 0.1% SDS at 72° C., dried, and subjected to autoradiography.

The result indicated that it was possible for all of (i), (ii), and (iii) to detect 0.031 μg of pBR 322 upon washing at 55° C., but that, upon washing at 65° C., (i) was mostly washed away, having failed to detect the positive signal hybridized with pRB 322, while (ii) and (iii) made it possible to detect the signals as in the case of washing at 55° C. In the washing at 72° C., all of (i), (ii), and (iii) failed to detect any signals. It has thus been proved in the hybridization experiment that the exchange from C to F strengthen the base pairing with G, resulting in the increase of Tm and the stabilization of the double-strand bond. It is meant by this fact that the exchange of C to F in the DNA probe makes it possible to carry out hybridization at higher temperatures, thus causing the formation of a novel and highly sensitive DNA probe without nonselective reaction.

EXAMPLE 8

Process according to the Nick translation method (a) Reagents used

*E. Coli* DNA polymerase I (50% glycerol solution, 5 units/ml was used: Boehringer Mannheim et al.); spleen DNase I [dissolved in 0.01 M hydrochloric acid in a ratio of 1 mg/ml, kept in storage at −20° C., and freshly diluted 1:10 with a diluent (10 mM Tris—HCl, pH 7.5, 5 mM MgCl₂, and 1 mg/ml bovine serum albumin), left standing at 0° C. for 2 hours to effect activation, and adjusted to have a final concentration of 0.14 mg/ml at the time of its use]; Nick translation buffer (10 times in volume, 500 mM Tris—HCl, pH 7.5, 50 mM MgCl₂, 10 mM 2-mercaptoethanol); dNTP solution (each 0.1 mM dTTP, dGTP, dATP, and pyridopyrimidine nucleoside-5'-triphosphate (dFTP) solution); and a sample DNA (λ phage Hind III fragment DNA dissolved in 10 mM Tris HCl, pH 7.5, 10 mM KCl, and 0.2 mM EDTA in a ratio of 1 μg/ml).

(b) Procedures (1) A mixture of 0.5 μl of Nick translation buffer, 10 μl of dDTP solution, 2 μl of sample DNA (1 μg/1 μl), and water making a total of 65 μl was vortexed.

(2) 5 μl of an activated DNase I solution was added thereto, left standing at room temperature for 2 hours, and nicking reaction was started. Then 2 μl of *E. Coli* DNA polymerase was added to the mixture and made to undergo a reaction at 14° C. for 1 hour.

(3) Thereafter, 35 μl of 0.25 M EDTA was added to the reaction mixture and heated at 68° C. for 10 minutes and the enzyme reaction was terminated. The reaction mixture was extracted two times with phenol and precipitated two times with ethanol. The final precipitate was dissolved in a mixture of 0.5 ml of 10 mM Tris—HCl, pH 7.5, 10 mM KCl, and 0.2 mM EDTA and the solution was kept in storage at −20° C. until the time of its use.

INDUSTRIAL APPLICATIONS

Oligo- or polynucleotides, which contain a pyridopyrimidine nucleotide derivative of the present invention and at least one pyridopyrimidine nucleotide derivative unit in the molecule or molecular terminal, can be used as the fluorescent DNA probe capable of forming base pairing in the studies on biopolymers, especially on the clarification of relationship between the structures and functions of proteins and nucleic acids, speedy identification of pathogenic microorganism, diagnosis of hereditary disorders and diseases, and also differentiation of normal cells from cancer cells.

We claim:

1. A pyridopyrimidine nucleotide derivative expressed by formula (I):

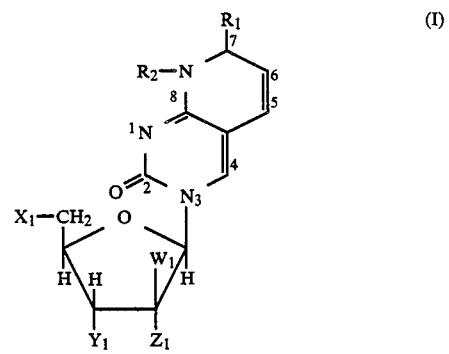

wherein $X_1$ and $Y_1$ each represent

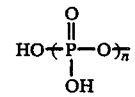

(wherein n is an integer of 0, 1, 2, or 3, provided that n is not 0 for both $X_1$ and $Y_1$);

wherein $Z_1$ represents a hydrogen atom or

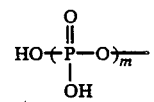

(wherein m is an integer of 0, 1, 2, or 3);

wherein $W_1$ represents a hydrogen atom or a hydroxyl group, provided that $Z_1$ is not

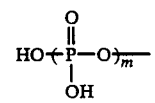

when $W_1$ represents a hydroxyl group; and wherein $R_1$ represents an amino group or halogen atom and $R_2$ represents a single bond between the carbon atom at the 7-position and the nitrogen atom at the 8-position or $R_1$ represents a carbonyl bond

formed with the carbon atom at the 7-position and $R_2$ represents a lower alkyl group.

2. The pyridopyrimidine nucleotide according to claim 1, wherein $X_1$ and $Y_1$ each represent

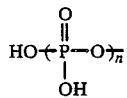

(wherein n is an integer of 1, 2, or 3);

wherein $Z_1$ represents a hydrogen atom or a hydroxyl group; and wherein $W_1$ represents a hydrogen atom.

3. An oligo- or polynucleotide which comprises at least one of a moiety having the structure:

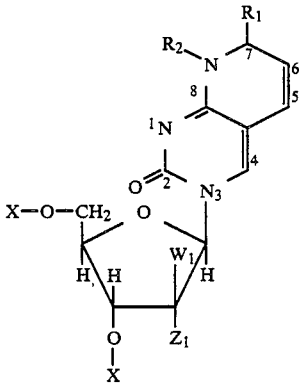

wherein X is hydrogen, a nucleotide or —PO$_3$H;
wherein $W_1$ represents a hydrogen atom or a hydroxyl group;
wherein $Z_1$ represents a hydrogen atom or a hydroxyl group;
however in no case do both $W_1$ and $Z_1$ represent a hydroxyl group;
wherein $R_1$ represents an amino group or halogen and $R_2$ represents a single bond between the carbon atom at the 7-position and the nitrogen atom at the 8-position or $R_1$ represents a carbonyl bond

formed with the carbon atom at the 7-position and $R_2$ represents a hydrogen atom or a lower alkyl group.

4. The oligo- or polynucleotide according to claim 3, wherein $Z_1$ represents a hydrogen atom and $W_1$ represents a hydrogen atom.

* * * * *